United States Patent [19]
Graff

[11] Patent Number: 5,316,146
[45] Date of Patent: May 31, 1994

[54] VIAL TRANSPORTER

[75] Inventor: Daniel A. Graff, Rhinebeck, N.Y.

[73] Assignee: Ulster Scientific, Inc., Milton, N.Y.

[21] Appl. No.: 665,077

[22] Filed: Mar. 6, 1991

[51] Int. Cl.⁵ ............................................. A61B 19/02
[52] U.S. Cl. .................................. 206/438; 206/446;
206/583; 206/591
[58] Field of Search ............... 206/591, 592, 594, 583,
206/806, 446, 438, 306

[56] References Cited

U.S. PATENT DOCUMENTS

| | | |
|---|---|---|
| 990,269 | 4/1911 | Howe . |
| 1,634,028 | 6/1927 | Ireland et al. ...................... 206/306 |
| 2,551,710 | 5/1951 | Slaughter ............................ 206/446 |
| 2,807,659 | 9/1957 | Woods ................................ 206/591 |
| 3,169,654 | 2/1965 | Pollklesner ......................... 206/591 |
| 3,283,894 | 11/1966 | Hafner et al. . |
| 3,338,390 | 8/1967 | Gordon .............................. 206/306 |
| 3,527,405 | 9/1970 | Harding ............................. 206/591 |
| 3,819,081 | 6/1974 | Runte ................................. 206/446 |
| 3,918,920 | 11/1975 | Barber . |
| 4,517,851 | 5/1985 | Tice . |
| 4,671,410 | 6/1987 | Hansson et al. . |
| 4,732,850 | 3/1988 | Brown et al. . |
| 4,746,017 | 5/1988 | Howard et al. . |
| 4,761,379 | 8/1988 | Williams et al. . |

FOREIGN PATENT DOCUMENTS 603611  4/1978  U.S.S.R. .............................. 206/592

*Primary Examiner*—Paul T. Sewell
*Assistant Examiner*—Thomas P. Hilliard
*Attorney, Agent, or Firm*—Sixbey, Friedman, Leedom & Ferguson

[57] ABSTRACT

A transport container for transporting fragile articles, such as test tubes or vials, which is able to accommodate vials of various sizes. The transport container protects the contents from forces or impact shocks associated with transport, thus preventing breakage of the vials. The transport container comprises a first body member including a spring for providing an axial bias force to a vial supported therewithin for restraining movement of the vial in a first axial direction and for urging the vial toward a second body member for proper seating therein. The second body member includes a plurality of positioning vanes which provide a yieldable restraint in a second axial direction and in the radial direction. The first and second body members are connected to form a releasable, liquid-tight seal and joint therebetween.

24 Claims, 3 Drawing Sheets

VIAL TRANSPORTER

TECHNICAL FIELD

The present invention relates to a container or package for the storage or transport of fragile articles. In particular, the invention relates to a transport container capable of holding various sizes of vials or test tubes, which may contain blood samples or other body fluids, and protecting the vials from breakage.

BACKGROUND

Often samples of body fluids, for example, blood, are taken from a patient for diagnostic or research purposes. Typically, such fluids are obtained in a doctor's office, hospital or clinic, in which lab facilities are either not available on the premises or are in a location remote from the place in which the sample is taken. In such circumstances, the sample must be transported to an appropriate lab facility for analysis and/or testing. Generally, a blood sample is placed in a vial or test tube for transport to the lab. The vials are normally inexpensive and not intended for the rigors of transport since they are generally discarded after each use to ensure that the samples are not contaminated by previous samples. A vial typically will include a tubular body with a plug type closure member which is inserted into the top of the tubular body and held therein by friction.

During transport, care must be taken to ensure that the vial is not broken, resulting in loss of the sample. Even slight cracking of the vial can expose the sample to impurities rendering the sample unusable or unreliable. Often, a number of samples are transported together. Breakage or leakage of any one sample will not only affect the broken or leaking sample, but also may jeopardize the integrity of the samples with which it is transported. In addition, the personnel (e.g., couriers, health care workers, etc.) handling such samples can be endangered by exposure to such body fluids.

When a sample is lost or contaminated, the doctor and patient both suffer great inconvenience in having to reschedule an appointment for drawing another sample. This can embarrass the doctor and the patient may lose confidence in the doctor and/or become discouraged by the discomfort associated with drawing a sample. These problems can be avoided by storing and/or transporting the sample in a container which prevents or minimizes breakage and leakage of the sample vial. The transport container should also be capable of containing leakage from the vial such that any leakage will be confined within the transport container.

Packages for preventing breakage of fragile articles are known in the health care field. For example, U.S. Pat. No. 3,283,894 to Hafner et al. discloses a packaging container for transportation of thin, fragile objects, such as thermometers. The package includes a tubular member with a pair of substantially identical end caps which are inserted at each end of the tube. The end caps include a plurality of thin, flexible ribs which extend along the length of each cap such that the thermometer is yieldably received in the end caps, with the ribs providing shock resistance. However, such a container is not suitable for transporting vials containing body fluids, such as blood vials. Aside from the size and shape differences between a package which is adapted to hold thermometers and one required for holding vials, the end caps of Hafner et al. are merely slid into the tube body and may easily become dislodged, thereby subjecting the contents to breakage and/or allowing liquid seeping from a leaking vial to escape from the transport container. In addition, since the Hafner et al. package utilizes flexible ribs which grasp the ends of the article they support, the ribs may grasp the pluglike closure of a fluid sample vial and inadvertently cause the body fluid-containing vial to be opened upon opening of the transport container, resulting in spilled or contaminated body fluid. During transport, the end caps could also become dislodged causing the plug closure to separate from the vial or subjecting the vial to impacts associated with transport.

U.S. Pat. No. 3,918,920 to Barber discloses a holder for sample containers, such as vials or test tubes. As with the Hafner et al. arrangement, Barber utilizes a plurality of ribs which yieldably support the sample container. However, rather than providing an enclosure for the container, Barber merely provides a holder for positioning test tubes or vials during testing by analytical instruments, with only a portion of the test tube or vial received within the holder. Thus, Barber does not provide a satisfactory container for transporting body fluid-containing vials, such as blood vials.

U.S. Pat. No. 4,671,410 to Hansson et al. discloses a medical package for the sterile storage of artificial implants in which the implant is housed within a capsule formed of the same material as the implant, and the capsule is positioned within a glass ampoule utilizing a spring which applies a biasing force in the axial direction of the ampoule. However, the use of an outer glass ampoule is unsatisfactory for transporting body fluid-containing vials, such as blood vials, since such an ampoule can easily be broken and, in addition, can be cost prohibitive, particularly when it is desired to discard the containers after each use.

Thus, notwithstanding the availability of various types of containers for supporting or housing vials or test tubes, there remains a need for a container for transporting vials or other body fluid-containing vessels which can prevent or minimize breakage or opening of the vials during transport. In addition, such a container should be able to confine fluid in such a manner that, even if the vial leaks, the leakage is confined within the transport container and thus will not endanger health care or delivery personnel and will not contaminate other samples transported therewith.

SUMMARY OF THE INVENTION

It is, therefore, an object of the present invention to provide a transport container for the storage and/or transport of fragile fluid-containing containers (hereinafter "fluid containers"), such as body fluid-containing vials, which prevents or minimizes breakage of the fluid containers during transport.

It is another object of the invention to provide a transport container which prevents or minimizes leakage from a fluid container during transport.

It is yet another object of the present invention to provide a transport container which can be utilized for transporting fluid containers of various sizes.

It is a further object of the present invention to provide a transport container which confines leaks from a fluid container, such that, even if the fluid container leaks, the leakage is maintained within the transport container.

It is a still further object of the invention to provide a transport container which provides yieldable restraints in radial and longitudinal directions of the transport container, such that a fluid container held therein is positioned away from the walls of the transport container, with the yieldable restraints absorbing shocks or impacts associated with transport.

It is a further object of the invention to provide a transport container formed of two parts, including a first part which provides a yieldable restraining support in the axial direction of the transport container and a second part having restraints which yieldably restrain the fluid container both in the radial direction and in the axial direction, thereby providing a yieldable restraint in all possible directions of movement of the fluid container.

It is a still further object of the invention to provide a transport container having a cap or cover provided with a spring which urges against the plug closure of a fluid container, thereby preventing impact of the fluid container with the top surfaces of the cap or cover while, at the same time, providing a biasing force to prevent dislodging of the fluid container plug closure from the fluid container and for properly seating the fluid container within other restraints of the transport container.

It is another object of the invention to provide a transport container in which a transport container member includes a plurality of vanes which are yieldable in the radial direction of the transport container, to absorb forces associated with transport and also to allow accommodation of fluid containers of various sizes, the vanes being preferably integral with the side walls and the bottom wall of the transport container and having less resiliency toward the bottom of the container, such that the vanes do not yield sufficiently to allow contact of the fluid container with the bottom wall of the transport container.

These and other objects and advantages are achieved in accordance with the present invention in which a transport container is provided for receiving a fluid container, such as a vial, with the transport container including first and second (cap and base) members. The second member or base is provided with a plurality of vanes which are preferably integrally molded with the transport container bottom wall and side walls and extend into the transport container second member from both the bottom wall and side walls for providing a yieldable support for the fluid container housed therewithin. The vanes yieldably restrain movement of the fluid container in both a first axial direction (i.e., toward the bottom wall of the second member) and in a radial direction (i.e., radially in the direction of the transport container side walls). A transport container first member (or cap) is provided having a spring integrally formed therewith, such that the spring biases the fluid container toward the vanes of the second member. By applying the biasing force to the top of the fluid container, dislodging of the plug closure (for example, in the event that the plug closure has not been properly inserted into the vial) is prevented. At the same time, the spring also prevents contact of the fluid container with the top wall of the first member (cap), such that breakage resulting from impact of the vial top wall with the transport container is prevented. In accordance with the present invention, the first and second members of the transporter are positioned in mutual sealing engagement during transport to provide a liquid-tight seal at their interface and any leakage from the fluid container is confined within the transporter.

Other objects and advantages of the present invention will become apparent from the following detailed description, when read in conjunction with the drawings.

DETAILED DESCRIPTION OF THE PREFERRED EMBODIMENT

Figure 1:
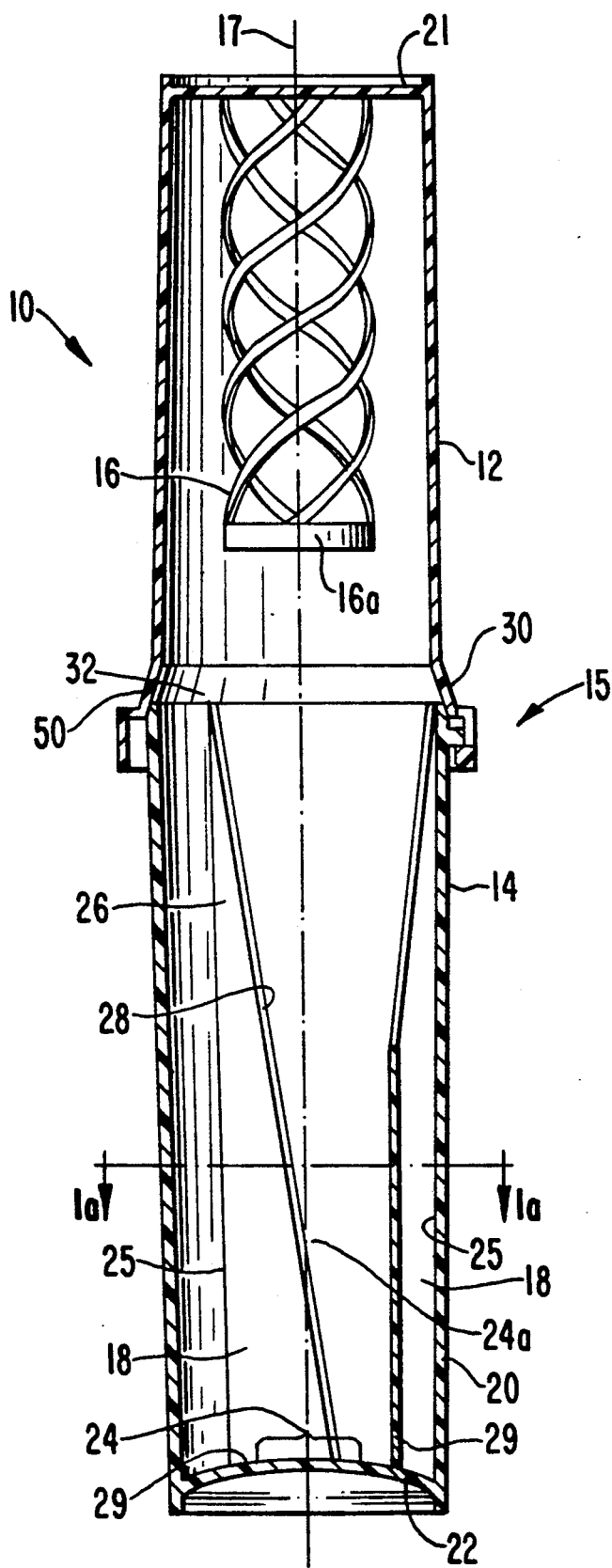
FIG. 1 illustrates a cross sectional view of a transport container in accordance with the present invention.

As shown in FIG. 1, the vial transporter 10 in accordance with the present invention includes a cap (transporter first member) 12 and a base (transporter second member) 14. The cap 12 and base 14 are releasably connected via a bayonet-type joint 15 and together form an elongated closed container having substantially tubular side or peripheral walls 20 and a longitudinally extending central axis 17. To simplify molding of the respective first and second members, 12, 14, each of the members tapers inwardly toward axis 17 from the end portion thereof adjacent the joint 15 to the end portion remote from joint 15.

Vial transporter 10 is adapted to receive, store and transport a vial 60 (see FIG. 3) within the closed container defined by cap 12 and base 14. In accordance with the present invention, vial transporter 10 includes means for axially and radially restraining movement of vial 60 when the transporter is shaken or subjected to impacts during storage or transport. Cap 12 includes a spring 16 extending within the cap from top wall 21 for axially restraining vial 60 against axially upward movement toward top wall 21 of cap 12, i.e., in the upward direction as shown in FIG. 1. Base 14 includes a plurality of positioning vanes 18 for radially restraining vial 60 against radial movement toward peripheral walls 20 and axially restraining vial 60 against movement toward bottom wall 22 of base 14, i.e., in the downward direction as shown in FIG. 1. In the preferred embodiments of this invention, the free end 16a of spring 16 engages the plug or closure 62 of vial 60 and biases it into the vial to prevent dislodging of the vial plug 62 and reduce the possibility that the fluid sample will leak from the vial. At the same time, the spring 16 biases vial 60 axially and downwardly to positively seat it within the positioning vanes 18 of base 14 and to thereby enhance the effectiveness of the vanes 18.

Figure 1A:
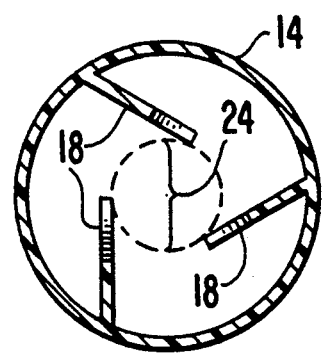
FIG. 1a illustrates a cross sectional view of the transport container taken along line I—I of FIG. 1.

Vanes 18 are desirably integrally molded with the transporter base 14 and are attached thereto along vane side and bottom edges, 25, 29, respectively, at both the side or peripheral wall 20 and bottom wall 22. The vanes 18 are yieldable and have a thickness which allows sufficient flexing to accommodate vials of various diameters. Thus, the vanes 18 will yield as necessary to accommodate the diameter of a vial 60 inserted within base 14. However, due to their attachment along bottom edges 29 to the bottom wall 22 of the transporter, relatively less yielding will occur along the portion of the vanes closest to the transporter bottom wall 22, while relatively more yielding will occur at the upper portions 26 of the vanes. As a result, vials of larger diameter are seated somewhat higher in the vanes, while vials of smaller diameter will be received more deeply within the vanes. In any case, the space 24 (see FIGS. 1 and 1a) defined centrally of the attachment of the vanes 18 along edges 29 with the bottom wall 22, is desirably small enough in diameter that even the smallest diameter vial which is to be carried will be prevented from sliding through the vanes and into contact with bottom wall 22 of the transporter. To assure that there is no contact with bottom wall 22, in some forms of the invention (see FIGS. 5 and 6) the transport container may optionally include raised arcuate members 80 disposed on the inside bottom wall of the container body member. Since the vanes 18 are molded integrally with the container bottom, it is generally preferable to utilize a small number of vanes, for example, three are shown in the FIG. 1 embodiment (see FIG. 1a), to allow the use of a less complicated mold. However, it is to be understood that in accordance with the present invention any number of vanes may be utilized, as desired.

Preferably, each vane 18 is generally triangular in shape, desirably formed as a substantially right triangle, having one side edge 25 extending along and attached to peripheral wall 20 and a second side edge 29 extending along and attached to bottom wall 22. The third side edge 28 (the hypotenuse in a right trianglular vane) extends between the ends of side edges 25 and 29. It slopes from the peripheral wall 20 generally toward the axis 17 of body 14 to aid in placing a vial 60 in the transporter, i.e., the side edge 28 of the vanes 18 acts as a ramp to direct the vial 60 towards the central space 24a between the vanes. Thus, a vial will, upon insertion into transporter base 14 initially contact vanes 18 at a point close to upper portions 26 and deflect the vanes as it is further inserted toward bottom wall 22 until the vanes can deflect no more, at which point they support, in basket-like fashion, the bottom of the vial. For this reason it will be appreciated that a relatively large diameter vial, upon insertion, will eventually find its basket-like support and be seated within the vanes closer to the upper portions 26 of the vanes than will a smaller diameter vial which will find its eventual support closer to bottom wall 22. While the vanes are yieldable and must deflect to accommodate various diameter vanes, they must also be sufficiently rigid that excessive radial deflection of the vanes is prevented to prevent contact of the vial with the side walls 20 of the transporter. Excessive radial deflection of the vanes is, in part, prevented by the rigidity achieved by attachment of the vanes along bottom edges 29 to the bottom wall 22 of the container.

The transporter 10 and integrally molded vanes 18 are desirably formed of a lightweight, easily moldable material such as polypropylene. Polypropylene having a thickness on the order of 0.010–0.030 inch will provide sufficient yieldability to absorb impact shocks and accommodate vials of various sizes, while providing sufficient rigidity to prevent contact of the vial with the transporter walls. Vane thicknesses of .012–.015 inch have been found particularly suitable.

The vanes 18 extend from and form an acute angle with respect to the peripheral side wall of the transport container (as particularly shown in FIG. 4 discussed hereinafter), such that upon insertion of a vial into the body, the vanes deflect toward the side wall which reduces the magnitude of the acute angle. As the vanes deflect, constrained by their bottom edges 29 and side edges 25 affixed to the container walls, they twist along their free surfaces, beginning at their top, to allow a substantial portion of the side surface of the vanes to contact the bottom and lower side surfaces of the vial. In this manner the vanes collectively form a basket which supports the vial and restrains it against movement in both the radial and axially downward directions. The smaller the vial, the more deeply it will be seated within the basket, since the vanes form a progressively narrower opening more deeply within the container. The use of three vanes is sufficient to form a stable three-point contact support; however, as discussed hereinafter, additional vanes may be provided.

Preferably, the top and bottom walls 21,22 of the transport container are inset from the ends of the container as shown in FIG. 1 and at least one of the walls is inwardly arcuate. The inset and inwardly arcuate walls provide additional flexing for yieldable support of the vials. More importantly, however, they tend to confine impact forces to the periphery of the container, where the wall strength is more effective in protecting/isolating the vial from the impact forces.

Figure 2:
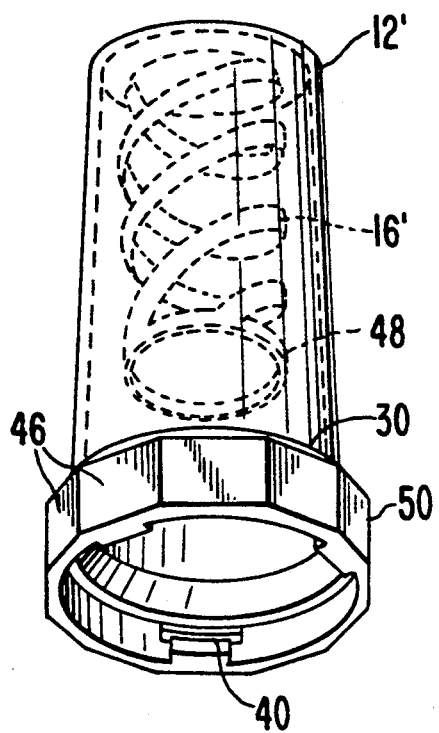
FIG. 2 illustrates a perspective view of a cap or first member for the transport container of the present invention.

As can best be seen in FIGS. 1 and 2, the transporter cap 12 is provided with an outwardly flared flange 50 circumferentially disposed about the end portion of cap 12 remote from top wall 21, the flange 50 including an outwardly tapered wall section 30 the inside diameter of which tapers to accommodate therewithin the outer diameter of the base 14 adjacent the bayonet joint 15. The transporter base 14 includes an inwardly tapered corresponding wall section 32 along the end portion of base 14 remote from bottom wall 22, the outer diameter of wall section 32 tapering to accommodate thereabout the inner diameter of the cap 12 with the two tapered wall sections 30,32 in mating, surface-to-surface contact. When the cap 12 and base 14 are locked in place, the bayonet joint 15 together with the mating tapered wall sections 30,32 form a liquid-tight seal, such that any fluid leaking from the vial will be contained within the transporter. This is important, even where breakage of the vial is prevented by the transporter, since leakage may occur due to reasons other than breakage of the vial. For example, the vial may have a crack due to manufacturing defects or mishandling of the vial prior to insertion into the transporter. In addition, the plug of the vial may be carelessly placed in the vial causing leakage to occur after placement of the vial in the transporter.

The inwardly tapered wall section 32 is preferably somewhat thinner than the remaining portions of the transporter side or peripheral walls in order that it may deformably engage the tapered wall section 30 to form a liquid-tight seal. If desired, a resilient sealing material (not shown) may also be placed between the tapered wall section 32 of the cap 12 and the tapered wall section 30 of the base 14 such that, when the cap and base are pressed together, the sealing material aids in forming a liquid-tight seal between the tapered walls 30,32.

Figure 3:
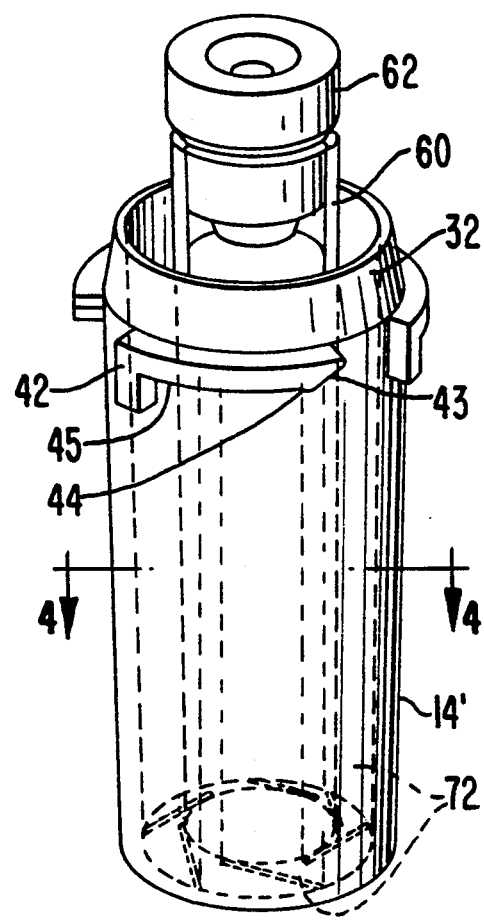
FIG. 3 illustrates a modified form of a base or second member of the transport container of the present invention.

As shown in FIG. 3, base 14' includes a bayonet member 42 comprising an incline 43 over which the mating lugs 40 on the cap 12' ride as the cap and base are relatively rotated to close the container. The incline 43 forces the cap 12 and base 14 closely together, thereby ensuring a liquid-tight seal between the respective tapered wall sections 30,32. The lug 40 is held in the closed position on a flat portion 45 of the bayonet member 42 and is prevented from accidentally riding back over the incline 43, which would inadvertently separate the cap and base, by a protruding corner 44 formed at the intersection of the incline 43 and the flat portion 45.

FIG. 2 shows a perspective view of a container cap 12' in accordance with the present invention. The spring 16' of FIG. 2 is somewhat simplified compared to spring 16 of FIG. 1, since only two helixes are utilized (whereas four are shown in FIG. 1) to simplify the mold necessary for forming the spring. As shown in FIG. 2, bayonet lugs 40 are provided which interlock with corresponding bayonet member 42 of the base 14'. As also shown in FIG. 2, the cap 12' includes a plurality of flat surfaces 46 about the periphery of the outwardly flared flange 50. These flat surfaces 46 prevent rolling of the transport container, for example, along and off a table to impact on the floor, and provide a convenient gripping area for closing and opening of the transporter to insert and remove the vial.

Still referring to FIG. 2, the spring 16' terminates at a ring-like member 48. The ring-like member 48 engages the top portion of the vial, or more desirably, the top closure plug 62 of the vial 60 to restrain axial upward movement of the vial and prevent the closure plug 62 from coming ajar. As the transport container 10 is closed with a vial 60 therewithin, the vial 60 is positively seated within the vanes 18 by the downward biasing of spring 16', such that the vanes 18 and bias spring 16' restrain movement of vial 60 and absorb impacts in both the radial and axial directions.

Figure 4:
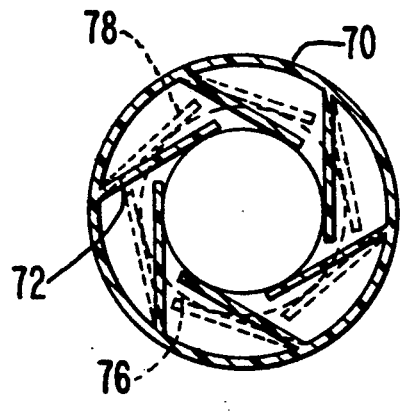
FIG. 4 illustrates a top sectional view of the transport container second member taken along line A—A of FIG. 3.

A modified form of the transporter base 14' with a vial 60 inserted therein is shown in FIGS. 3 and 4. The third side edges 28 of vanes 72 provide a slight biasing force for centering the vial and preventing axially downward movement of the vial toward the container bottom wall 22. In the embodiment of FIGS. 3 and 4, six vanes 72 are utilized, in contrast to the three-vane embodiment of FIG. 1. The vanes are disposed at an acute angle with respect to the peripheral wall 70 of the base 14', as shown in FIG. 4, such that insertion of the vial 60 causes rotational, yieldable movement and deflection of the vanes 72 toward the wall 70. Excessive rotation of the vanes toward the wall is prevented by the connection of the vanes to the bottom wall 22 of the container. The vanes may extend along substantially the entire height of the container base member 14', as shown in FIG. 3, or may extend only along a portion of the height of base member 14. In FIG. 4, a relatively small diameter vial is shown in solid lines, with the vanes 72 only slightly deflected. A somewhat larger diameter vial (as shown by the broken lines 76) will cause the vanes to deflect to a larger extent to accommodate the larger vial, as shown in broken lines at 78.

Figure 5:
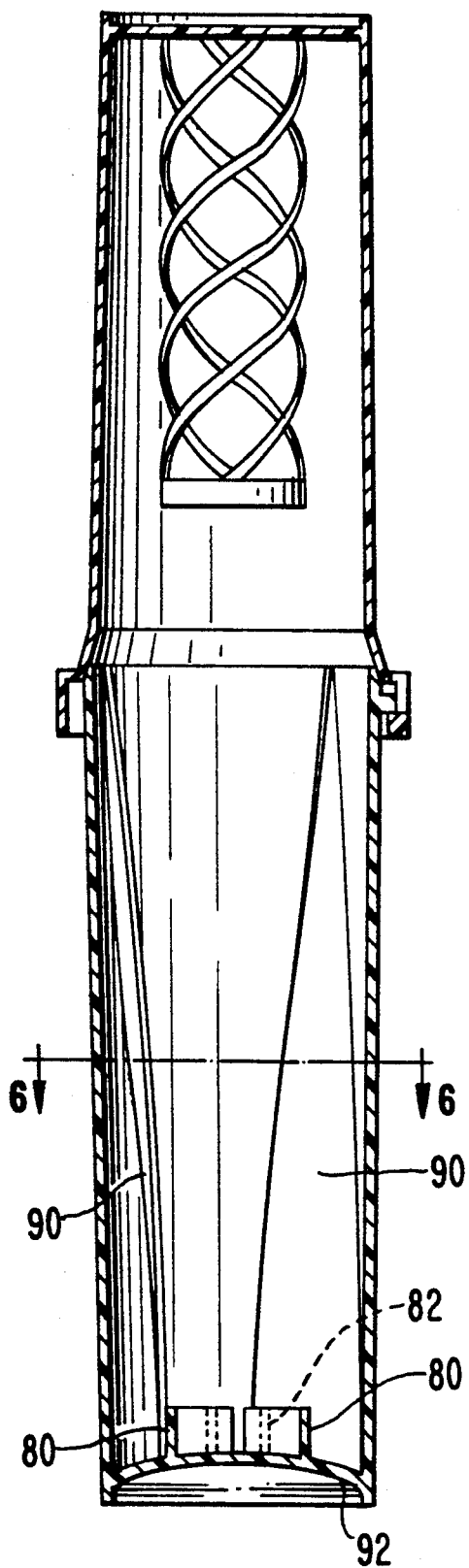
FIG. 5 illustrates a cross-sectional view of an alternate embodiment of a transport container in accordance with the present invention.
Figure 6:
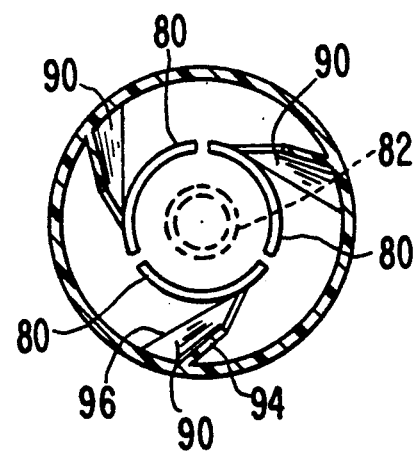
FIG. 6 illustrates a top sectional view of the transport container second member taken along line B—B of FIG. 5 and showing an optional additional center restraint added.

Another embodiment of the present invention is illustrated in FIGS. 5 and 6. In this embodiment the vanes 90 curve about the periphery of the container side wall as they extend from their upper end toward the bottom wall 92, such that the vanes take on a helical or spiral form. As shown in FIG. 6, the radial width 96 of the vanes at the bottom of the container is greater than the radial width 94 of the vanes nearer their top. The helical form of the vane requires a slightly more complicated mold; however, the ability of the vanes to form a basket-like support is improved, since a greater portion of the side surfaces of the vanes is presented to and contacts the bottom and lower side wall portions of the vial. The progressively widening, spiraling vanes, from top to bottom of the base, form progressively narrower seating positions from top to bottom, acting somewhat like an iris, with progressively smaller diameter vials seated progressively lower along the length of the vanes in the container.

As shown in the embodiments of FIGS. 5 and 6, the transport container may optionally include arcuate members 80 disposed on the inside bottom wall 92 of the container body member. The arcuate members 80 extend in an arcuate path between the affixed bottom edges of adjacent vanes and collectively form a generally circular in cross-section, raised cup-like support to define a lower limit of movement for vials inserted within the body member. The cup-like support limits the extreme axial depth to which a vial may be seated within the transport container and is preferably formed with appropriate dimensions and is desirably formed as a split ring to allow it to yield and absorb impacts associated with transport. Thus, the arcuate members 80 provide additional assurance that the vials inserted into the container of the present invention will not be seated in contact with the container bottom wall 92. In addition, the arcuate members 80 limit the degree of flexing of the vanes, such that the arcuate members 80 act as an additional radial as well as axial restraint on a vial supported within the container. It is to be understood that the use of the arcuate members is not limited to the helical vane embodiments of FIGS. 5 and 6 and may also be utilized with the embodiments illustrated in FIGS. 1, 3 and 4.

As shown in FIG. 6, a more centrally disposed cup support (shown in broken lines at 82) may be provided in addition to, or in lieu of, the supports 80. The centrally disposed support 82, taking the form in a preferred embodiment of a raised cylinder seated upon bottom wall 92, acts as an axial limit for vial insertion, and has relatively little effect in limiting vane flexure. The centrally disposed support 82, however, is particularly effective in preventing contact of the vials with the bottom wall 92 of the container. This is the case since it can effectively prevent contact with the bottom wall even when vials smaller than a recommended size range are inserted. As with the arcuate members 80, the central support 82 may also be utilized in the embodiments of FIGS. 1, 3 and 4 if desired.

INDUSTRIAL APPLICABILITY

The transport container of the present invention is particularly useful for transporting vials, such as vials containing body fluids, in such a manner that the chances of breaking or spilling the contents of the vials are substantially reduced. In addition, even if the contents of the vial inadvertently escape, the transport container of the present invention is designed to contain any leakage within the transporter. The transporter can be injection-molded of a number of suitable materials, for example polypropylene. Since the transporter requires only two molded pieces, it can be formed inexpensively and, if desired, it may be discarded after each use. In addition, if desired, the vanes and/or spring elements may be formed separately from the container body and adhered or affixed to the interior of the transport container.

In use, a vial containing body fluid to be transported is inserted into the base of the vial transporter. The cap is then placed over the transporter body, urged downwardly and rotated, forming a liquid-tight seal between the cap and base of the transporter by virtue of the bayonet joint and the tapered wall sections of the cap and base. With the cap locked on to the body, the spring restrains axially upward movement of the vial and also prevents dislodging of the plug closure from the vial. At the same time, the spring urges and maintains the vial in a seated position within the vanes in the base, thus providing yieldable axial and radial positioning. When the vial is subjected to an external force or subjected to sharp impacts, for example if the transporter or package containing the transporter is dropped, or if other articles are suddenly dropped on top of the transporter, the impacts are absorbed by the transporter walls and by resilient supports in all possible directions of vial movement.

While particular embodiments have been described, it is to be understood that these embodiments are not to be construed as limiting the scope of the present invention, as other modifications are possible. The scope of the present invention is therefore to be construed in accordance with the appended claims.

What is claimed is:

1. A transport container for transporting fragile fluid containers, the transport container comprising:
    an elongated body having first and second ends and side wall means, said first and second ends and said side wall means defining an openable closed container for receiving said fluid container therewithin;
    means for accessing the interior of said closed container for allowing insertion and removal of said fluid container;
    a plurality of yieldably deflectable vanes in said transport container for accommodating the diameter of a fluid container inserted into said transport container between said vanes, said vanes attached to said side wall means and said second end and extending inwardly from a portion of said side wall means and said second end into said transport container, said vanes each including an inclined edge portion extending substantially along the entire length of said vane and having a width, measured along each vane from said side wall means toward the longitudinal axes of said transport container, which is greater for portions of each said vane adjacent said second end wall than for portions of said vanes along said axis remote from said second end wall, said vanes yieldably restraining movement of said fluid container in a direction toward said second end and supporting said fluid container along its bottom and lower side surfaces within said transport container with the end of said fluid container adjacent to and spaced from said second end of said transport container, said vanes also spacing said fluid container from and yieldably restraining movement thereof toward said side wall means; and
    bias means in said transport container for spacing said fluid container from and restraining movement of said fluid container toward said first end and for applying a biasing force to said fluid container in a direction away from said first end and toward said second end for seating said fluid container within said plurality of vanes;
    whereby a fluid container received within the transport container is maintained out of contact with said first and second ends and said side wall means by the cooperative interaction of said bias means and said plurality of vanes.

2. The transport container of claim 1, wherein said bias means includes a spring associated with said first end.

3. The transport container of claim 2, wherein said spring comprises a helical spring formed integral with said first end.

4. The transport container of claim 3, wherein said vanes are integral with said second end.

5. The transport container of claim 4, wherein said vanes are integral with said side wall means.

6. The transport container of claim 1, wherein said side wall means are substantially tubular and wherein said vanes are generally helically disposed within said closed container.

7. The transport container of claim 1, wherein said accessing means comprises side wall means formed in two separable parts, said side wall means comprising first side wall portions associated with said first end and second side wall portions associated with said second end, and releasable connector means for releasably connecting said first and second side wall portions for allowing separation of said side wall means for insertion and removal of said fluid container and for forming said closed container for storage or transport, said releasable connector means forming a liquid-tight seal between said first and second side wall portions.

8. The transport container of claim 7, wherein each of said first and second wall portions includes a tapered wall section at the end portions thereof adjacent said releasable connector means, said sections mating for forming said liquid-tight seal upon interconnection of said first and second wall portions by said releasable connector means.

9. The transport container of claim 8, wherein the tapered wall section at the end portion of said second wall portion is thinner than the remainder of the second wall portion for deformably engaging the tapered wall section at the end portion of said first wall portion.

10. The transport container of claim 8, wherein said first side wall portion includes a plurality of flat surfaces around the periphery thereof for preventing rolling of said transport container.

11. The transport container of claim 1, wherein at least one of said first and second ends includes an end wall bowed inwardly toward said opposite end wall.

12. The transport container of claim 1, wherein the portions of said vanes closest to said second end yieldably deflect less than the portions of said vanes more remote from said second end.

13. The transport container of claim 1, further including a first raised generally tubular member on said second end, said member disposed between said vanes and extending from said second end toward said first end.

14. The transport container of claim 13, wherein said first raised member comprises a plurality of adjacent, spaced apart, raised arcuate portions, each said arcuate portion having opposite ends, the ends of each portion being spaced from the ends of adjacent portions for defining a generally tubular member having a split peripheral wall.

15. The transport container of claim 14, wherein said first raised member has a generally circular cross section in a plane perpendicular to the longitudinal axis of said transport container.

16. The transport container of claim 13 further including a second raised generally tubular member on said second end, said second member disposed within the peripheral wall of said first raised member.

17. The transport container of claim 7, wherein each vane is generally triangular in shape.

18. The transport container of claim 1, wherein the portions of said vanes closest to said second end yieldably deflect less than the portions of said vanes more remote from said second end.

19. An elongate transport container for transporting elongate fragile articles, the transport container comprising:

first and second elongate body members releasably connectable to form a closed container for receiving said fragile articles therewithin;

said first body member including a first end wall;

a spring formed integral with and positioned within said first body member;

a plurality of yieldable vanes formed integral with and positioned within said second body member, said second body member including a second end wall and side wall means, said vanes integrally attached to said second end wall and said side wall means and extending from said second end and side wall means into said second body member, said vanes each including an inclined edge portion extending substantially along the entire length of said vane and having a width, measured along each vane from said side wall means toward the longitudinal axis of said elongate container, which is greater for portions of each said vanes adjacent said second end wall than for portions of said vanes axially remote from said second end wall; and releasable connecting means associated with said first and second body members for allowing separation of said first and second body members for insertion and removal of said fragile articles and for connecting said first and second body members for storage or transport, said connecting means forming a liquid-tight seal between said first and second body members;

said spring spacing said fragile articles from said first end wall and providing a yieldable impact absorbing restraint in a first axial direction, and said vanes spacing said fragile articles from said second end wall and said side walls and providing a yieldable impact absorbing restraint in a radial direction and a second axial direction, whereby a fragile article inserted within said second body member and closed within said container by said first body member is seated within said vanes by said spring of said first body member urging said fragile article toward said second end wall.

20. The transport container of claim 19, wherein said spring is a helical spring.

21. The transport container of claim 19, wherein said releasable connecting means includes tapered wall sections associated with said first and second body members adjacent said releasable connecting means, said respective tapered sections mating to form a liquid-tight seal upon connection of said first and second body members by said releasable connecting means.

22. The transport container of claim 19, further including a first raised generally tubular member extending from said second body member end wall toward said first body member for defining a lower limit for insertion of fragile articles into said second body member, said raised member having a generally circular cross section in a plane perpendicular to the longitudinal axis of said transport container.

23. The transport container of claim 22, wherein said end wall of said second body member bows inwardly toward said end wall of said first body member.

24. The transport container of claim 22 further including a second raised generally tubular member on said second end, said second member disposed within the peripheral wall of said first raised member.

* * * * *